United States Patent
Li et al.

(10) Patent No.: US 10,267,741 B2
(45) Date of Patent: Apr. 23, 2019

(54) METHOD FOR IMPROVING DETECTIVE SENSITIVITY ON CARBON ELEMENT IN LASER-INDUCED BREAKDOWN SPECTROSCOPY

(71) Applicant: Huazhong University of Science and Technology, Wuhan, Hubei (CN)

(72) Inventors: Xiangyou Li, Hubei (CN); Jiaming Li, Hubei (CN); Lianbo Guo, Hubei (CN); Xiaoyan Zeng, Hubei (CN); Yongfeng Lu, Hubei (CN); Zhongqi Hao, Hubei (CN); Ran Zhou, Hubei (CN); Yun Tang, Hubei (CN); Ping Yang, Hubei (CN)

(73) Assignee: HUAZHONG UNIVERSITY OF SCIENCE AND TECHNOLOGY, Wuhan, Hubei (CN)

( * ) Notice: Subject to any disclaimer, the term of this patent is extended or adjusted under 35 U.S.C. 154(b) by 0 days.

(21) Appl. No.: 16/035,072

(22) Filed: Jul. 13, 2018

(65) Prior Publication Data

US 2018/0335388 A1  Nov. 22, 2018

Related U.S. Application Data

(63) Continuation-in-part of application No. PCT/CN2017/112766, filed on Nov. 24, 2017.

(30) Foreign Application Priority Data

Dec. 29, 2016 (CN) ............. 2016 1 1247163

(51) Int. Cl.
  *G01J 3/30* (2006.01)
  *G01N 21/71* (2006.01)
  (Continued)

(52) U.S. Cl.
  CPC ............. *G01N 21/718* (2013.01); *G01J 3/10* (2013.01); *G01N 21/6402* (2013.01); *G01N 21/75* (2013.01)

(58) Field of Classification Search
  CPC ............. G01N 21/718; G01N 21/645; G01N 21/6458; G01J 3/4406; G01J 3/02
  (Continued)

(56) References Cited

U.S. PATENT DOCUMENTS 6,407,811 B1 * 6/2002 Snyder ............... G01J 3/443
                                                    356/316
7,955,855 B2   6/2011 Rothschil et al.
(Continued)

FOREIGN PATENT DOCUMENTS

CN  103604781 A  2/2014
CN  103792215 A  5/2014
(Continued)

OTHER PUBLICATIONS

International Search Report (English and Chinese) and Written Opinion issued in PCT/CN2017/112766, dated Feb. 26, 2018, total 10 pages.
(Continued)

*Primary Examiner* — Md M Rahman
(74) *Attorney, Agent, or Firm* — Hamre, Schumann, Mueller & Larson, P.C.

(57) ABSTRACT

The present invention belongs to the field of laser plasma emission spectrometry, and in particular relates to a method for improving the detection sensitivity on a carbon element in laser-induced breakdown spectroscopy. The method specifically comprises the following steps: ablating the surface of a sample to be tested by using a laser beam emitted so as to rapidly heat the surface of the sample and the ambient air close to the surface of the sample into plasma, atomize
(Continued)

carbon in the sample and nitrogen in the ambient gas, and combine carbon with the nitrogen into C—N radicals; tuning a wavelength-tunable laser to a wavelength needed by stimulated absorption transition of C—N radicals, and outputting a laser beam to radiate the plasma so that stimulated absorption transition of C—N radicals is carried out, then fluorescent signals are emitted with spontaneous radiative transition; collecting and recording an emission fluorescence spectrum of the C—N radicals; and qualitatively or quantitatively analyzing on carbon element. By adopting the method provided by the invention, in a case of hardly affecting the matrix spectrum, C—N radical signal can be enhanced in high selectivity, thereby avoiding the interference generated by the matrix, and spectrum signals of the carbon element in the plasma can be enhanced, thereby improving the detective sensitivity of LIBS on carbon element.

4 Claims, 3 Drawing Sheets

(51) Int. Cl.
  *G01J 3/10* (2006.01)
  *G01N 21/64* (2006.01)
  *G01N 21/75* (2006.01)
(58) Field of Classification Search
  USPC ....................................................... 356/318
  See application file for complete search history.

(56) References Cited

U.S. PATENT DOCUMENTS

2008/0245964 A1* 10/2008 Miles .................... G01N 22/00
                                                              250/288
2011/0313407 A1* 12/2011 Rafailov ................ A61N 5/062
                                                              606/2

FOREIGN PATENT DOCUMENTS

| CN | 105067592 A | 11/2015 |
|----|-------------|---------|
| CN | 105486676 A | 4/2016 |
| CN | 106770191 A | 5/2017 |

OTHER PUBLICATIONS

Abdulmadjid, et al., "Sensitive analysis of carbon, chromium and silicon in steel using picosecond laser induced low pressure helium plasma", ELSEVIER, ScienceDirect, Spectrochimica Acta Part B, vol. 114, Dec. 1, 2015, pp. 1-6.
Pan et al., "Quantitative Analysis of Carbon Steel with Multi-Line Internal Standard Calibration Method Using Laser-Induced Breakdown Spectroscopy", Spectroscopic Technique, Applied Spectroscopy, vol. 70 issue 4, pp. 702-708, first published online Feb. 12, 2016; Issue published Apr. 1, 2016.

\* cited by examiner

METHOD FOR IMPROVING DETECTIVE SENSITIVITY ON CARBON ELEMENT IN LASER-INDUCED BREAKDOWN SPECTROSCOPY

BACKGROUND OF THE PRESENT INVENTION

Field of the Present Invention

The present invention belongs to the field of laser plasma emission spectrometry, and particularly relates to a method for improving the detection sensitivity on a carbon element in laser-induced breakdown spectroscopy (LIBS), which is capable of enhancing spectra signals of the carbon element in the plasma and improving the detective sensitivity of the LIBS on a carbon element.

Description of the Related Art

Laser-induced breakdown spectroscopy (LIBS) is an atomic emission spectral analysis technique. The basic principle of this technique is that a pulsed laser beam is used to ablate the surface of a sample to generate plasma, and elemental information about the species and content contained in the sample is obtained by collecting and analyzing the emission spectrum of the plasma. Due to characteristics such as all-element detection as well as rapid, real-time, on-line, and remote analysis, the LIBS keeps receiving extensive attention from researchers all around the world in these years.

However, due to the special structure of carbon atoms, their spectral lines in the plasma are very weak, easily interfered by the spectrum of the matrix, and mainly concentrated in the vacuum ultraviolet (VUV) region that is greatly absorbed by air, which places high demands on the optical acquisition system. Therefore, researches on carbon detection by LIBS mainly focus on samples with high carbon contents, such as coal, plastics and biological tissues. For samples with low carbon contents, the detection of a carbon element has always been the difficulty in LIBS. At present, there are mainly two methods for detecting trace amount of carbon using LIBS: 1) a method in which the entire light path is protected by noble gas to avoid the absorption of carbon spectrum in the VUV by the air and improve spectral acquisition efficiency. For example, a low pressure helium environment was used in S. N. Abdulmadjid et al. (Spectrochimical Acta Part B, 2015, 114: 1-6). This method is suitable for carbon detection in the laboratories, needs gas refilling operation when the sample is changed, and cannot achieve the gas protection of the whole spectrum collection light path in the remote detection and the like, which results in a great limitation in the industrial field detection applications; and 2) a method in which a multi-element spectrum correction algorithm is used to derive the carbon content. For example, a multi-spectral internal standard algorithm was used in C. Y. Pan et al. (Applied Spectroscopy, 2016, 70(4): 702-708). This method uses the spectra of multiple elements to compensate the interfered spectrum of the carbon element from the perspective of later experimental data processing. However, this method is limited by other elements in the sample and is only suitable for detection of samples with the same matrix.

Due to the above defects in the prior art, there is an urgent need to solve this problem, i.e., to design a method for detecting the carbon content by LIBS, which is capable of avoiding the influence of the matrix spectrum on the carbon element spectrum and improving the detective sensitivity of LIBS on the carbon element.

SUMMARY OF THE PRESENT INVENTION

In view of the above-described problems, the present invention provides a method for improving the detection sensitivity on a carbon element in LIBS, in which a laser beam is used to ablate a sample such that carbon in the sample reacts with nitrogen in the ambient gas to produce C—N radicals (usually, the spectral intensity of the C—N radicals is weak) and resonant excitation of the C—N radicals is carried out by using a wavelength-tunable laser to obtain fluorescence signals of the C—N radicals. With this method, in a case of hardly affecting the matrix spectrum, a C—N radicals signal can be enhanced in high selectivity, thereby overcoming the interference generated by the matrix, and spectra signals of the carbon element in the plasma can be enhanced, thereby improving the detective sensitivity of the LIBS on the carbon element.

In order to achieve the above objective, according to an aspect of the present invention, there is provided a method for improving the detection sensitivity on a carbon element in a LIBS, comprising:

S1: preparing a sample to be tested, turning on a wavelength-fixed laser to output a laser beam, and ablating the surface of the sample to be tested using the laser beam, so that under the ablation of the laser beam, the surface of the sample to be tested and the ambient gas close to the surface of the sample to be tested are rapidly heated into plasma, carbon contained in the sample to be tested and nitrogen in the ambient gas are atomized in the plasma, and carbon atoms and nitrogen atoms in the plasma are combined into C—N radicals;

S2: tuning a wavelength-tunable laser to a specific wavelength required for stimulated absorption transition of electrons of the C—N radicals, and outputting a laser beam by using the wavelength-tunable laser to irradiate the plasma so as to carry out resonant excitation of the electrons of the C—N radicals in the plasma;

S3: after the electrons of the C—N radicals in the plasma are excited to carry out energy level transition and then emit fluorescence signals, collecting and recording a fluorescent spectrum emitted when spontaneous radiative transition of the electrons of the C—N radicals in the plasma is carried out; and S4: according to the emission fluorescent spectrum of the C—N radicals in the plasma collected in the step S3, qualitatively or quantitatively analyzing the carbon element in the sample to be tested to obtain a detection result of the carbon element.

Preferably, in the step S2, when the wavelength of the laser beam of the wavelength-tunable laser is tuned, target electronic state is in bands of the C—N radicals is first selected, an appropriate spectral line is selected as an excited line according to the target electronic state, and then the wavelength of the wavelength-tunable laser is tuned to be the same as the selected excited line.

By detecting the emission spectrum of the C—N radicals in the plasma instead of the carbon atomic spectrum in the conventional LIBS, and by detecting the spectral intensity of the C—N radicals to represent the carbon content, it is possible to avoid the use of carbon atomic lines in the deep ultraviolet band that is susceptible to air absorption, and spectral lines of the C—N radicals in the visible light band are used to improve the detective sensitivity on carbon.

Moreover, by selecting appropriate target excitation electrons and excited line, an emission spectrum of the C—N radicals with a high intensity can be obtained for subsequent analysis of the carbon element.

Preferably, in the step S2, when the plasma is irradiated with the laser beam, nitrogen is blown into the plasma to increase the reaction efficiency of the combination between the carbon atoms and the nitrogen atoms.

A number of comparative experiments showed that through nitrogen blowing during the irradiation, the reaction efficiency of carbon atoms and nitrogen atoms can be effectively increased, and the generation rate of the C—N radicals can be increased, thereby obtaining an emission spectrum of the C—N radicals with a higher intensity.

Preferably, in the step S4, a carbon element quantitative analysis model is established based on the proportional relation between the spectral intensity of the C—N radicals and the carbon content in the sample to qualitatively or quantitatively analyze the carbon element in the sample to be tested.

The mechanism of action of the carbon element detection method for improving the sensitivity of the LIBS of the present invention is:

the surface of a sample to be tested is ablated by using a laser beam emitted from a laser so as to rapidly heat the surface of the sample and the ambient air close to the surface of the sample into plasma, atomize carbon in the sample and nitrogen in the ambient gas in the plasma, and combine the carbon element with the nitrogen into C—N radicals; and a wavelength-tunable laser is tuned to a wavelength required for stimulated transition of electrons of the C—N radicals, and a laser beam is outputted to radiate the plasma. When the single photon energy of the irradiation laser is equal to the gap between two energy levels in the C—N radicals, electrons at the lower energy level are stimulated to transit up to the upper energy level, and then spontaneously transit down to the upper energy level due to the instability, so that fluorescence is emitted. In addition, the emission fluorescent spectrum of the C—N radicals are collected and recorded, then carbon in the sample is qualitatively or quantitatively analyzed based on the proportional relation between the spectral intensity of the C—N radicals and the carbon content in the sample, so that the detective sensitivity of LIBS on the carbon element can be improved.

In general, compared with the prior art, the present invention has the following beneficial effects:

(1) in the method of the present invention, by detecting the emission spectrum of the C—N radicals in the plasma instead of the spectrum of the carbon element in the conventional LIBS, detecting the spectral intensity of the C—N radicals to represent the carbon content and irradiating the plasma with a wavelength-tunable laser beam to selectively excite the C—N radicals in the plasma, the other spectral lines of the plasma emission spectrum are hardly affected, and the interference of the spectral lines of the matrix can be effectively reduced, which reduces the matrix effect. Meanwhile, the C—N radical signals are enhanced in high selectivity, which improves the detective sensitivity of LIBS on the carbon element.

(2) in the method of the present invention, through detection of the C—N radical spectrum in the visible range instead of the carbon atom spectrum in the deep ultraviolet range to make up for the insufficiency that the optical acquisition system has a low acquisition efficiency in the deep ultraviolet range, the carbon element detective sensitivity is improved. Since spectral lines of the C—N radicals in the visible light range are used instead of carbon atomic lines in the deep ultraviolet range that is susceptible to air absorption, the light path system does not require vacuum or noble gas protection.

(3) in the method of the invention compared with the vacuum or noble gas protection method, the sample can be quickly changed and industrial online and remote analysis can be achieved. Moreover, in this method, a wavelength-tunable laser is used as a carbon spectrum enhancement tool, and compared with existing methods, advantages of the LIES such as remote detection, online analysis and solid-liquid-gas state indifferent analysis in the atmospheric environment are retained.

(4) in the method of the invention, a wavelength-tunable laser beam is directly irradiated on the plasma, which has little modification to the light path, does not destroy the advantages of the laser probe detection and can achieve the detection of a carbon element in a laboratory or an industrial scene.

DETAILED DESCRIPTION OF THE EMBODIMENTS

Figure 1:
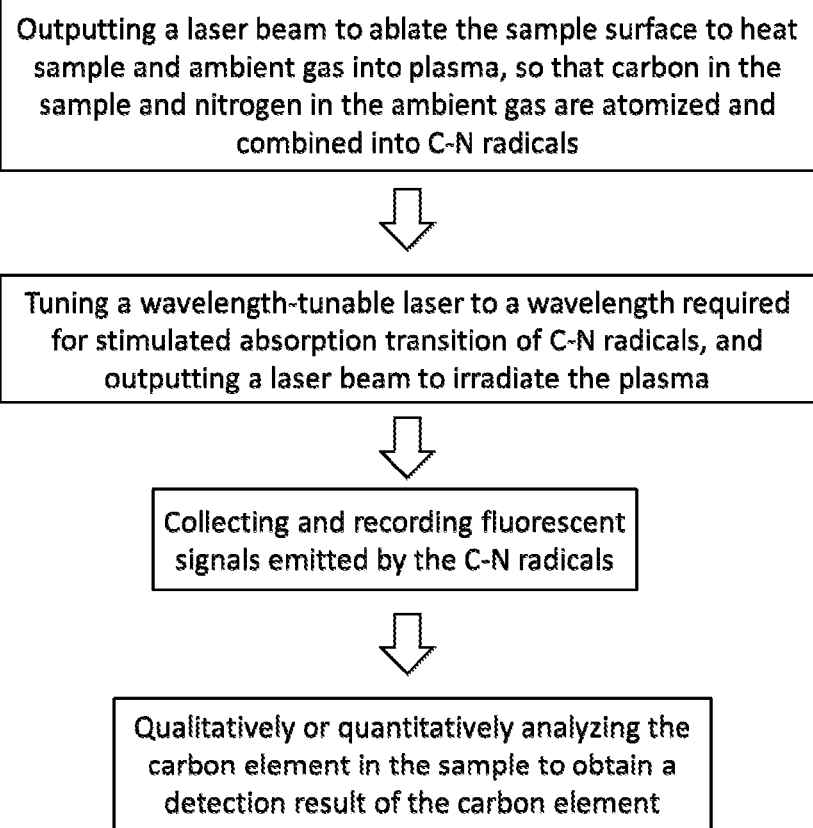
FIG. 1 is a flowchart of a method according to the present invention.

For clear understanding of the objectives, features and advantages of the present invention, detailed description of the present invention will be given below in conjunction with accompanying drawings and specific embodiments. It should be noted that the embodiments described herein are only meant to explain the present invention, and not to limit the scope of the present invention.

The invention provides a method for improving the detective sensitivity on carbon element in LIBS, the principle of which is that an emission spectrum of C—N radicals generated by reaction of carbon in the sample to be tested with nitrogen in the ambient gas is used instead of a carbon atom spectrum in the traditional laser probe, and then a wavelength-tunable laser beam is used to irradiate the plasma so that the C—N radicals are selectively excited and then emit fluorescent signals. The method specifically includes the following steps:

S1: preparing a sample to be tested, turning on a wavelength-fixed laser to output a laser beam, and ablating the surface of the sample to be tested using the laser beam, so that under the ablation of the laser beam, the surface of the sample to be tested and the ambient gas close to the surface of the sample to be tested are rapidly heated into plasma, carbon contained in the sample to be tested and nitrogen in the ambient gas are atomized in the plasma and carbon atoms and nitrogen atoms in the plasma are combined into C—N radicals;

S2: tuning a wavelength-tunable laser to a specific wavelength required for stimulated absorption transition of electrons of the C—N radicals, and outputting a laser beam by using the wavelength-tunable laser to irradiate the plasma so as to carry out resonant excitation of the electrons of the C—N radicals in the plasma;

S3: after the electrons of the C—N radicals in the plasma are excited to carry out energy level transition and then emit fluorescence signals, collecting and recording a fluorescent spectrum emitted when spontaneous radiative transition of the electrons of the C—N radicals in the plasma is carried out; and S4: according to the emission fluorescent spectrum of the C—N radicals in the plasma collected in the step S3, qualitatively or quantitatively analyzing the carbon element in the sample to be tested by establishing a mathematical model so as to obtain a detection result of the carbon element.

In a preferred embodiment of the present invention, in the step S2, when the wavelength of the laser beam of the wavelength-tunable laser is tuned, target excitation electrons in an energy band of the C—N radicals are first selected, an appropriate spectral line is selected as an exciting line according to the target excitation electrons, and then the wavelength of the wavelength-tunable laser is tuned to be the same as the selected exciting line.

In another preferred embodiment of the present invention, in the step S2, when the plasma is irradiated with the laser beam, nitrogen is blown into the plasma to increase the reaction efficiency of the carbon atoms and the nitrogen atoms.

In another preferred embodiment of the present invention, in the step S4, a carbon element quantitative analysis model is established based on the proportional relation between the spectral intensity of the C—N radicals and the carbon content in the sample to qualitatively or quantitatively analyze the carbon element in the sample to be tested.

For better description of the present invention, three specific embodiments are given below.

Embodiment 1

This method will be described in detail by taking the example of detecting carbon in polyvinyl chloride.

The polyvinyl chloride plastic with a carbon content of 38.7 wt. % is selected as a sample.

For lasers, the Brilliant laser from Quantel Inc. in French and the Vibrant wavelength-tunable laser from OPOTEK Inc. in USA are selected, and for a spectrometer, the SCT320 spectrometer from Princeton Instrument Inc. is selected. Electrons of C—N radicals at the vibration energy level $v=0$ in the electronic level $X^2\Sigma$ are selected as excitation target, a spectral line of 388.3 nm at (0, 0) in the violet system $B^2\Sigma$-$X^2\Sigma$ of the C—N radicals is selected as an excited line, and the wavelength-tunable laser is tuned such that a laser beam with a wavelength of 388.3 nm can be outputted.

This method specifically includes the following steps:

(1) turning on the Brilliant laser to output a laser beam, and ablating the surface of the polyvinyl chloride sample with the laser beam, so that plasma is generated on the surface of the polyvinyl chloride sample, carbon in the polyvinyl chloride and nitrogen in the air are atomized in the plasma, and carbon atoms and nitrogen atoms are combined into C—N radicals;

(2) turning on the wavelength-tunable laser to output a laser beam with a wavelength of 388.3 nm, and irradiating the plasma with the laser beam to resonantly excite electrons of C—N radicals in the vibrational level $v=0$ in the electronic level $X^2\Sigma$, so that the electrons of C—N radicals transit up to vibrational level $v=0$ in the electronic level $B^2\Sigma$ with stimulated absorption; and (3) collecting and recording fluorescent signals emitted when spontaneous radiation transition of the electrons of C—N radicals in the vibrational level $v=0$ in the electronic level $B^2\Sigma$ to the vibrational level $v=1$ in the electronic level $X^2\Sigma$ is carried out.

Figure 2:
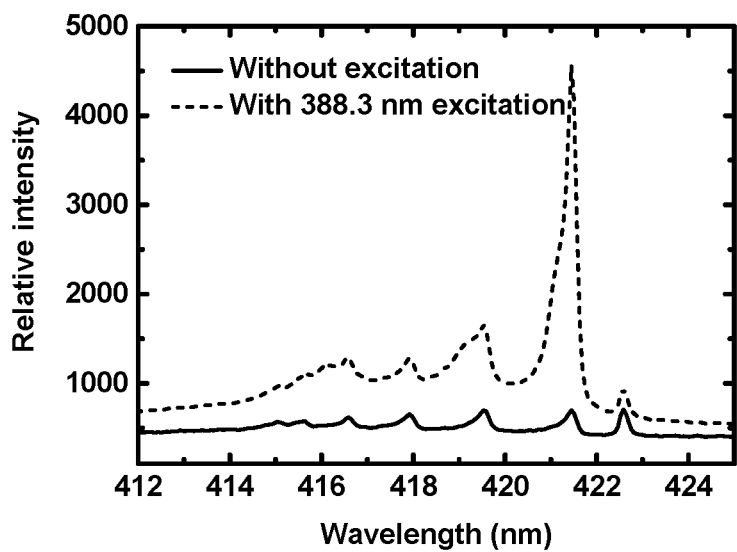
FIG. 2 is a spectrogram of the C—N radicals in the polyvinyl chloride in an embodiment 1 of the present invention.

As shown in FIG. 2, a weak 421.6 nm spectrum of the C—N radicals can be observed without the 388.3 nm laser irradiation, and a 421.6 nm spectrum of the C—N radicals with a higher intensity can be observed with the 388.3 nm laser irradiation.

In conclusion, by adopting the method of the present invention, the spectrum of the carbon element in the laser probe can be dramatically enhanced in high selectivity, and the detection sensitivity of LIBS on the carbon element in the polyvinyl chloride can be improved.

Embodiment 2

This method will be described in detail by taking the example of detecting carbon in the soil.

The petroleum-contaminated soil with a petroleum content of 10 wt. % is selected as a sample.

For lasers, the Ultra50 laser from Bigsky Inc. in USA and the Vibrant wavelength-tunable laser from OPOTEK Inc. in USA are selected, and for a spectrometer, the SCT320 spectrometer from Princeton Instrument Inc. is selected. Electrons of C—N radicals in the vibrational level $v=1$ in the electronic level $X^2\Sigma$ are selected as excitation target, a spectral line of 421.6 nm at (0, 1) in the violet system $B^2\Sigma$-$X^2\Sigma$ of the C—N radicals is selected as an excited line, and the wavelength-tunable laser is tuned such that a laser beam with a wavelength of 421.6 nm can be outputted.

This method specifically includes the following steps:

(1) turning on the Ultra50 laser to output a laser beam, and ablating the surface of the soil sample with the laser beam, so that plasma is generated on the surface of the soil sample, carbon in the soil and nitrogen in the air are atomized in the plasma, and carbon atoms and nitrogen atoms are combined into C—N radicals;

(2) turning on the wavelength-tunable laser to output a laser beam with a wavelength of 421.6 nm, and irradiating the plasma with the laser beam to resonantly excite electrons of the C—N radicals in the in the vibrational level $v=1$ in the electronic level $X^2\Sigma$, so that C—N radicals transit up to the vibrational level $v=0$ in the electronic level $B^2\Sigma$ with stimulated absorption; and (3) collecting and recording fluorescence signals emitted when spontaneous radiation transition of the electrons of the C—N radicals in the vibrational level $v=0$ in the electronic level $B^2\Sigma$ to the vibrational level $v=0$ in the electronic level $X^2\Sigma$ is carried out.

Figure 3:
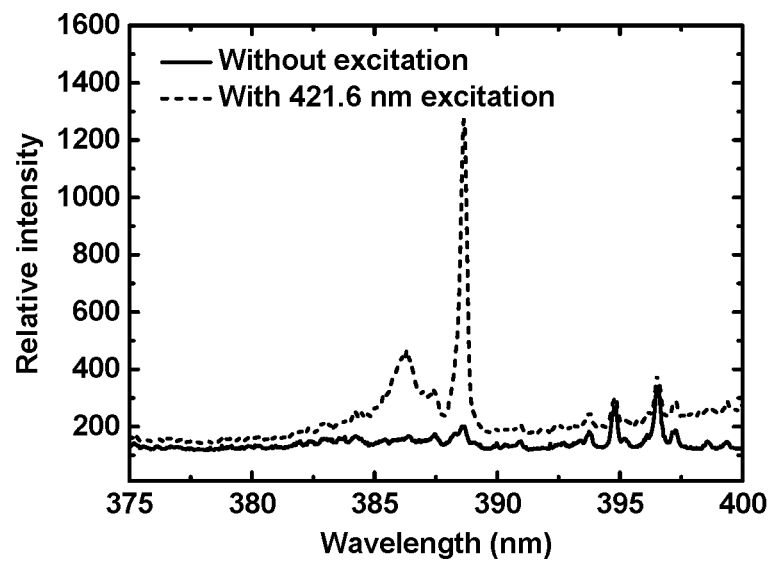
FIG. 3 is a spectrogram of the C—N radicals in a petroleum-contaminated soil sample in an embodiment 2 of the present invention.

As shown in FIG. 3, a weak 388.3 nm spectrum of the C—N radicals can be observed without the 421.6 nm laser irradiation, and a 388.3 nm spectrum of the C—N radicals with a higher intensity can be observed with the 421.6 nm laser irradiation.

In conclusion, by adopting the method of the present invention, the spectrum of the carbon element in the laser probe can be dramatically enhanced in high selectivity, and the detection sensitivity of LIBS on oil contamination in the soil can be improved.

Embodiment 3

This method will be described in detail by taking the example of detecting carbon in the steel.

A set of seven pig iron samples (national certified material GSB03-2582-2010) with carbon contents of 2.16 wt. % to 4.12 wt. % are selected as samples.

For lasers, the Nimma400 laser from Beamtech China and the Vibrant wavelength-tunable laser from OPOTEK Inc. in USA are selected, and for a spectrometer, the SCT320 spectrometer from Princeton Instrument Inc. is selected. Electrons of C—N radicals in the vibrational level v=1 in the electronic level $X^2\Sigma$ are selected as excitation target, a spectral line of 421.6 nm at (0, 1) in the violet system $B^2\Sigma$-$X^2\Sigma$ of the C—N radicals is selected as an excited line, and the wavelength-tunable laser is tuned such that a laser beam with a wavelength of 421.6 nm can be outputted.

This method specifically includes the following steps:

(1) turning on the Nimma400 laser to output a laser beam, and ablating the surface of a pig iron sample with the laser beam, so that plasma is generated on the surface of the pig iron sample, carbon in the pig iron and nitrogen in the air/nitrogen are atomized in the plasma and carbon atoms and nitrogen atoms are combined into C—N radicals;

(2) turning on the wavelength-tunable laser to output a laser beam with a wavelength of 421.6 nm, and irradiating the plasma with the laser beam to resonantly excite electrons of the C—N radicals in the vibrational level v=1 in the electronic level $X^2\Sigma$, so that the electrons of the C—N radicals transit up to the vibrational level v=0 in the electronic level $B^2\Sigma$ with stimulated absorption; and (3) collecting and recording fluorescent signals emitted when spontaneous radiation transition of the electrons of the C—N radicals in the vibrational level v=0 in the electronic level $B^2\Sigma$ to the vibrational level v=0 in the electronic level $X^2\Sigma$ is carried out.

Figure 4:
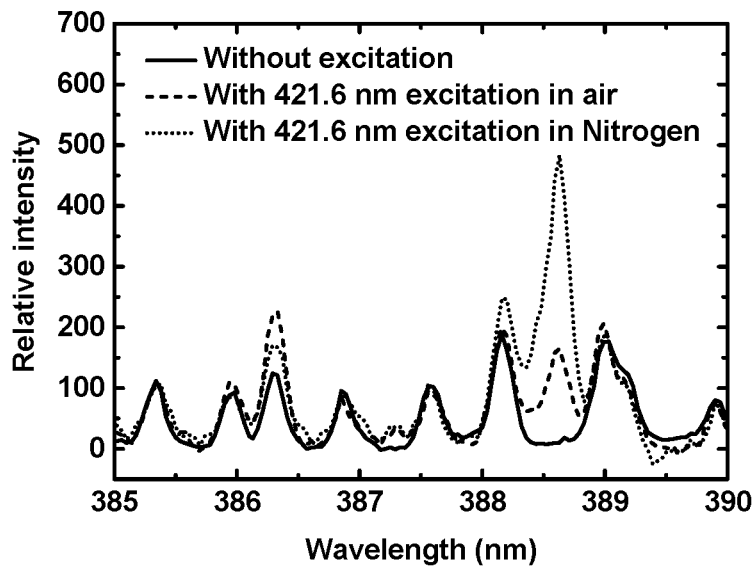
FIG. 4 is a spectrogram of the C—N radicals in a pig iron sample in an embodiment 3 of the present invention.
Figure 5:
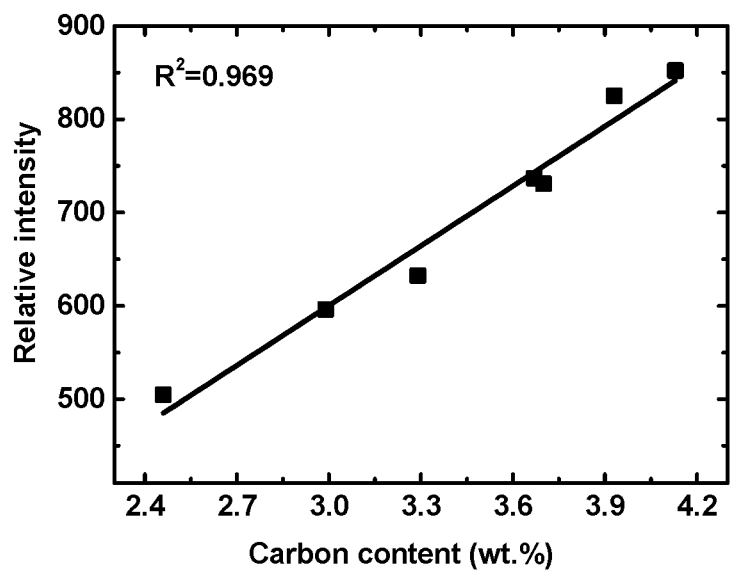
FIG. 5 is a graph showing the relationship between the spectra intensity of the C—N radical fluorescence plotted in the embodiment 3 of the present invention and the carbon content.

As shown in FIG. 4, a 388.3 nm spectrum of the C—N radicals cannot be observed without the 421.6 nm laser irradiation, and a 388.3 nm spectrum of the C—N radicals with a higher intensity can be observed with the 421.6 nm laser irradiation. Nitrogen blowing into the plasma can improve the reaction efficiency of the carbon atoms and the nitrogen atoms, further enhance the 388.3 nm spectrum of C—N radicals, and improve the detective sensitivity. As shown in FIG. 5, by plotting the spectra intensity of the C—N radical fluorescence and the carbon content, a carbon element quantitative analysis model can be established.

In conclusion, by adopting the method of the present invention, the spectrum of the carbon element in the laser probe can be dramatically enhanced in high selectivity, the detection sensitivity of LIBS on the carbon element in the steel can be improved, and the qualitative and quantitative analysis of a carbon element in the steel can be achieved.

While particular embodiments of the present invention have been shown and described, it will be obvious to those skilled in the art that changes and modifications may be made without departing from the spirit and scope of the present invention.

The present invention claimed is:

1. A method for improving the detective sensitivity on carbon element in LIBS, comprising:

step S1: preparing a sample to be tested, turning on a wavelength-fixed laser to output a laser beam, and ablating the surface of the sample to be tested using the laser beam, so that under the ablation of the laser beam, the surface of the sample to be tested and the ambient gas close to the surface of the sample to be tested are rapidly heated into plasma, carbon contained in the sample to be tested and nitrogen in the ambient gas are atomized in the plasma, and carbon atoms and nitrogen atoms in the plasma are combined into C—N radicals;

step S2: tuning a wavelength-tunable laser to a specific wavelength required for stimulated absorption transition of electrons of the C—N radicals, and outputting a laser beam by using the wavelength-tunable laser to irradiate the plasma so as to carry out resonant excitation of the electrons of the C—N radicals in the plasma;

step S3: after the electrons of the C—N radicals in the plasma are excited to carry out energy level transition and then emit fluorescence signals, collecting and recording a fluorescent spectrum emitted when spontaneous radiative transition of the electrons of the C—N radicals in the plasma is carried out; and step S4: according to the emission fluorescent spectrum of the C—N radicals in the plasma collected in the step S3, qualitatively or quantitatively analyzing the carbon element in the sample to be tested to obtain a detection result of the carbon element.

2. The method of claim 1, wherein in the step S2, when the wavelength of the laser beam of the wavelength-tunable laser is tuned, excitation target in an energy band of the C—N radicals are first selected, an appropriate spectral line is selected as an excited line according to the excitation target, and then the wavelength of the wavelength-tunable laser is tuned to be the same as the selected exciting line.

3. The method of claim 1, wherein in the step S2, when the plasma is irradiated with the laser beam, nitrogen is blown into the plasma to increase the reaction efficiency of the carbon atoms and the nitrogen atoms.

4. The method of claim 3, wherein in the step S4, a carbon element quantitative analysis model is established based on the proportional relation between the spectral intensity of the C—N radicals and the carbon content in the sample to qualitatively or quantitatively analyze the carbon element in the sample to be tested.

* * * * *

UNITED STATES PATENT AND TRADEMARK OFFICE
CERTIFICATE OF CORRECTION

PATENT NO. : 10,267,741 B2  
APPLICATION NO. : 16/035072  
DATED : April 23, 2019  
INVENTOR(S) : Li et al.

Page 1 of 1

It is certified that error appears in the above-identified patent and that said Letters Patent is hereby corrected as shown below:

On the Title Page

The following inventor should be deleted:
"Yongfeing LU"

Signed and Sealed this  
Fifth Day of May, 2020

Andrei Iancu  
*Director of the United States Patent and Trademark Office*